US006033374A

United States Patent [19]

Miller, Jr.

[11] Patent Number: 6,033,374

[45] Date of Patent: Mar. 7, 2000

[54] PENILE TRACTION DEVICE

[76] Inventor: Stanley J. Miller, Jr., 2794 Noble Fir Ct., Woodbridge, Va. 22192

[21] Appl. No.: 09/004,296

[22] Filed: Jan. 8, 1998

[51] Int. Cl.[7] .......... A61F 5/40

[52] U.S. Cl. .......... 602/36; 602/61; 602/70; 128/883; 482/105

[58] Field of Search .......... 602/36, 38, 70, 602/32, 61; 482/105, 44, 79, 93; 128/842, 844, 883, 918, DIG. 15; 600/38, 39, 41; 604/347, 351, 353; 606/241

[56] References Cited

U.S. PATENT DOCUMENTS

| | | | |
|---|---|---|---|
| 19,814 | 3/1858 | Monestier . | |
| 2,723,663 | 11/1955 | Davis | 602/36 |
| 3,297,026 | 1/1967 | Van Pelt | 128/878 |
| 3,561,434 | 2/1971 | Kilbey | 602/36 |
| 3,751,031 | 8/1973 | Yamauchi . | |
| 3,863,638 | 2/1975 | Rogers, III et al. . | |
| 4,269,179 | 5/1981 | Burton et al. | 602/36 |
| 4,368,883 | 1/1983 | Titkin . | |
| 4,407,276 | 10/1983 | Bledsoe | 128/DIG. 15 |
| 4,422,455 | 12/1983 | Olsen | 128/878 |
| 4,544,155 | 10/1985 | Wallenbrock et al. | 482/139 |
| 4,713,067 | 12/1987 | Rothenberg et al. | 604/353 |
| 4,971,074 | 11/1990 | Hrubetz . | |
| 5,074,291 | 12/1991 | Carter . | |
| 5,184,629 | 2/1993 | Erickson et al. . | |
| 5,235,975 | 8/1993 | Gang et al. | 607/108 |
| 5,599,275 | 2/1997 | France | 600/38 |
| 5,618,302 | 4/1997 | Martin | 602/61 |
| 5,632,726 | 5/1997 | Repice et al. . | |
| 5,702,330 | 12/1997 | De Monbrun et al. | 482/105 |
| 5,707,341 | 1/1998 | Mathewuse | 600/39 |
| 5,797,890 | 8/1998 | Goulter et al. | 604/351 |

*Primary Examiner*—Richard J. Apley
*Assistant Examiner*—Victor Hwang
*Attorney, Agent, or Firm*—Clyde I. Coughenour

[57] ABSTRACT

The penile traction device includes a preferably reusable or disposable foam pressure dissipation friction pad having a preferably felt-like backing positioned around the penile shaft for dissipating applied force and frictionally holding the device to the shaft. A weight supporting means has a strap that surrounds and transfers force to the pressure dissipation friction pad. The weight support strap receives force from a selective weight means. A resilient and/or shock absorbing connector can be placed between the weight support means and selective weight means. A two-section weight relief means is also connected to the selective weight means. A handle on the relief means allows the patient or attendant to manually lift all or a part of the weight from the weight support means. The two sections of the relief means are adjustable to vary the overall length of the relief means. By attaching a support loop on one end of the relief means to a belt or other support and adjusting the overall length of the relief means, the amount of force transferred from the weights to the weight support means can be incrementally adjusted by transferring a portion of the force to the belt or other support.

18 Claims, 2 Drawing Sheets

PENILE TRACTION DEVICE

BACKGROUND OF THE INVENTION

1. Field of the Invention

A penile traction device is disclosed. A foam pad surrounds the penile shaft and, through a flexible support means, applies a traction force created by weights. A relief device is also included for removing all or a portion of the force.

2. Description of Related Art

Operations necessitated by diseases, such as Peyronie's disease are frequently performed and penile enlargement operations, often referred to as augmentation phalloplasty, are becoming popular with many men. These procedures involve removal and/or modification of body material. In one procedure, fat and fascia are removed from the gluteal area and transferred to the penile shaft. As an alternative, dermis and fat are removed from the fold area at the bottom of the buttock and transferred to one or both sides of the penile shaft. As much as one-third of the total penile length can be inside the body and not visible. A portion, up to about two inches, of the penile shaft, can be made visible by cutting or severing the ligament that connects the base of the penis to the pubic bone. After the ligament is severed, a portion of the penile shaft, previously out of view, can be seen. The visible length of the penile shaft can also be increased by cutting the fold or web of skin that is attached to the base of the penile shaft or a Z-plasty can be performed there to extend or loosen the supporting web of skin in that area.

When one of these operations or procedures is performed, the healing process includes scarring and other contracture in the area the surgery was performed. To prevent contraction, weights are attached to the penile shaft. This use of weights prevents contraction and, to some extent, is believed to assist visible extension of the penile shaft. The principal process now used to attach these weights is to thread a rubber tube through the weights with the rubber tube placed around the penile shaft to apply the weight along the penile shaft, stretching the shaft and applying tension to any healing sutures made to or above the shaft. Even though the tube and weights are only applied for periods of about ten minutes, the tube tends to block blood flow. This "strangles" the lower portion of the penile shaft and the action of applying weight in a relatively small area restricting blood flow and pinching is painful and medically dangerous.

The attachments of weights to body parts for traction and exercise has been in use for a century with J. Monestier, U.S. Pat. No. 19,814, issued Mar. 30, 1858, and G. Tiktin, U.S. Pat. No. 4,368,883, issued Jan. 18, 1983, and P. Carter, U.S. Pat. No. 5,074,291, issued Dec. 24, 1991, examples. The attachment of sheaths, for urine collection, prosthetic devices, prophylactic devices, sexual aid devices, etc., is common with C. Rogers, U.S. Pat. No. 3,863,638, issued Feb. 4, 1975, and M. Hrubetz, U.S. Pat. No. 4,971,074, issued Nov. 20, 1990 and R. Erickson et al, U.S. Pat. No. 5,184,629, issued Feb. 9, 1993, examples. The use of adjustable weights and attachments for traction are common with P. Carter above, and N. Yimauchi. U.S. Pat. No. 3,751,031, issued Aug. 7, 1973 and R. Repice, U.S. Pat. No. 5,632,726, issued May 27, 1997, examples.

SUMMARY OF THE INVENTION

The present invention overcomes the problems of the prior art by dissipating the force over an extensive area of the penile shaft, permitting blood flow, providing for shock absorption, incremental force regulation, and manual emergency force relief. A preferably high density, hypoallergenic foam pad is wrapped around the penile shaft with a weight supporting means around it. A resilient, flexible shock absorbing connector can be used to transfer force to the weight supporting means from a weight means. While the primary control is by selection of the weights attached to the weight means, a two section weight relief means is provided for manually taking all or a part of the weight off of the weight supporting means and for incrementally dissipating portion of the force off of the weight supporting means by transferring it to a belt or other support for the relief means. The amount of force transferred is set by adjusting the length of the relief means extending between the belt or other support and the weight means. The overall length is set by adjusting the location at which the first and second sections of the weight relief means are secured together.

DESCRIPTION OF THE PREFERRED EMBODIMENTS

Figure 4:
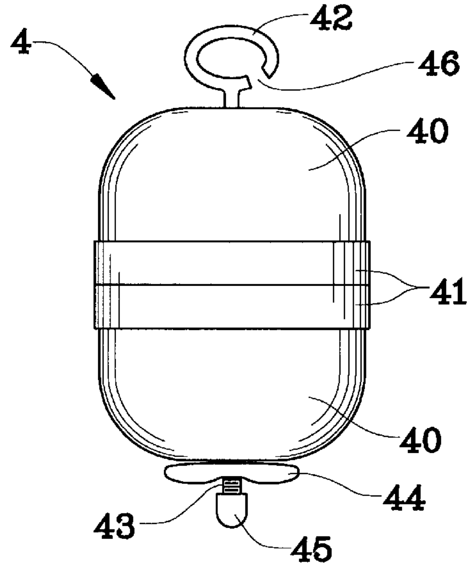
FIG. 4 is a side view of the selective weight means.
Figure 1:
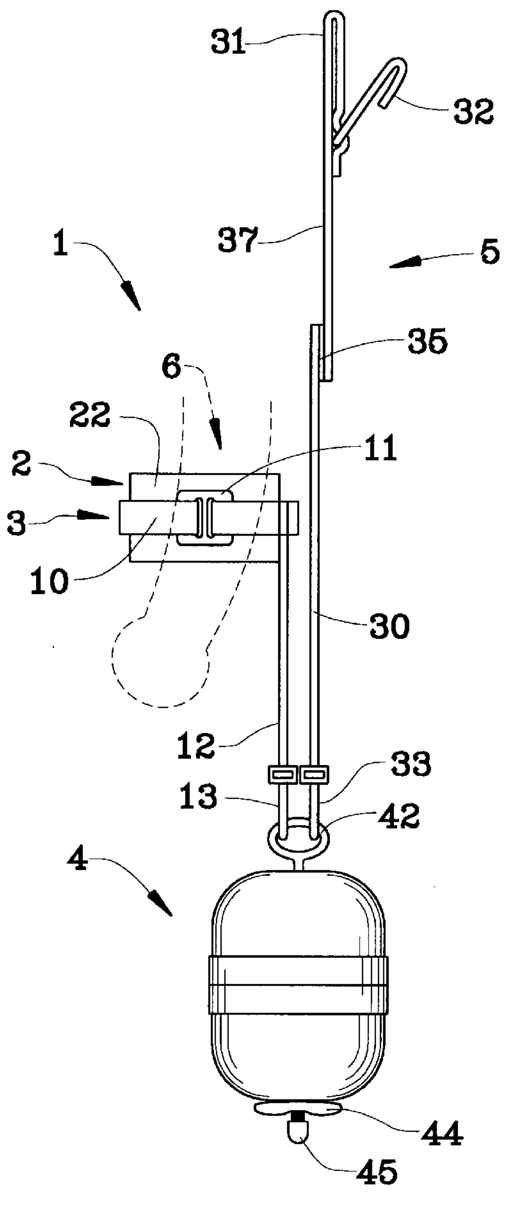
FIG. 1 is a side view of the traction device in its in-use configuration.
Figure 2:
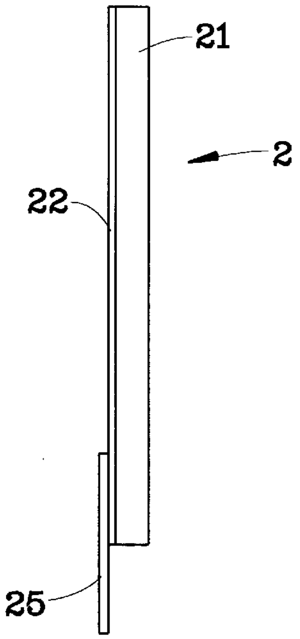
FIG. 2 is a side view of the pressure dissipation friction pad means of the traction device.
Figure 5:
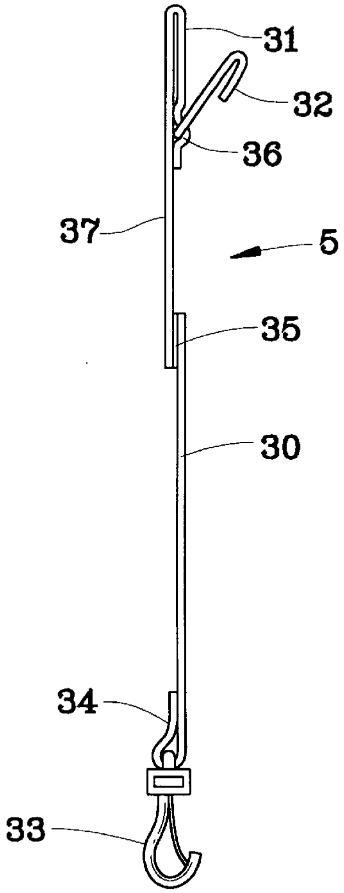
FIG. 5 is a side view of the weight relief means of the traction device.

FIG. 1 shows the components of the traction device 1 assembled in their in-use configuration, as attached to a penile shaft 6, with a selective weight device 4, best shown in FIG. 4, causing traction of the shaft and any incisions made to or above it. A pressure dissipation and friction pad device 2, best shown in FIG. 2, is held in place around the shaft by a weight support device 3, best shown in FIG. 3. A weight attachment strap 10 of the weight supporting device is threaded through a strap "buckle" 11 to tighten the strap 10 around the pressure dissipation and friction pad device 2 to assure that it is held in place. The weight support device 3 is attached to the selective weight device 4 by attaching the weight hook 13 to the eye 42 of the selective weight device eye bolt 43. The weights are provided with central holes, for passage of a bolt 43, and the weights are held on the bolt using a wing nut 44 with a rubber cap 45 used over the threads of the bolt end, to prevent damage to the flesh or clothing of the patient or adjacent objects. A adjustment strap relief or weight relief device 5, best shown in FIG. 5, provides an emergency relief means and means for controlling the amount of weight pulling on the weight support device 3 and penile shaft. An adjustment strap 30 is attached to the selective weight device eye 42 of the eye bolt 43 by relief weight hook 33. The adjustment strap 30 is secured to an auxiliary support strap 37 by a hook and loop type connection including a hook securing pad 35. The auxiliary support strap 37 is bent back upon itself to form a strap handle 31 and to secure in place a support loop 32. In an emergency the strap handle can be grabbed and lifted so as to take all the weight off of the support device 3 and penile shaft 6. A portion only of the weight can be taken off or relieved from the support device 3 by securing the support loop 32 over a belt or other attachment or support means and adjusting the length of the weight relief means between the support loop 32 and relief weight hook 33, by moving upwardly or downwardly the place the adjustment strap connects with the auxiliary support strap. The hook securing pad 35 of the adjustment strap 30 and the auxiliary support strap 37 are secured together by having a plurality of the hooks of the hook pad 35 attached to the auxiliary support strap or a loop pad cover on it. By adjusting the position the adjustment strap 30 is attached to the auxiliary support strap 37, any desired amount of weight can be taken off of support device 3 and the penile shaft and dissipated or diverted to the belt or other support used to secure the support loop 32. By adjustment of the relief device, traction forces intermediate the weights available for the weight support device, or comfort adjustments, can be made by the patient or attendant. The amount of weight applied to the penile shaft can vary from one-quarter pound to more than ten pounds. The time the weight is applied to the penile shaft can vary from one minute to more than 15 minutes. The time is usually determined by the physician or care giver taking into consideration the amount of weight to be applied, the proximity to the surgical procedure, the amount of traction determined to be needed, the pain or comfort threshold of the patient, etc.

Because the patient is often mobile while the traction is taking place, any movement creates an inertia force, primarily on the weights. Examples are walking, going up or down stairs and standing up. A sudden movement can cause excruciating pain, rupture of stitches or even separate the dissipation and friction pad from the penile shaft. By using flexible yielding connectors and/or an elastic band device or strap to attach the weight, a shock-absorbing function can be performed. This is shown in FIG. 1 by a resilient and/or elastic, flexible connector 12 attached to the support device 3.

FIG. 2 shows a side view of the pressure dissipation friction pad device 2. Its main component is a porous high-density hypo-allergenic foam rubber or plastic pad 21 that is from about ⅛ to ¾ inch thick, from about 1 to 3 inches wide, and from about 6 to 9 inches long. A felt-like or other similar backing 22, that can be made from nylon fibers for example, is provided as the foam pad 21 is rather flexible, easily torn, and does not readily receive and hold a securing means, such as the multiplicity of small hooks commonly used in loop-hook securing. It has been found that a felt-like backing is sturdy enough to extend the force exerted by the weight attachment strap 10 over the foam pad and penile shaft even when the weight attachment strap 10 does not extend over the full width of the foam pad 21. The hooks used in the common hook-loop securing means adhere well to the felt-like material. The backing 22 is preferably coextensive with the foam pad 21. The pressure dissipation friction pad 2 can be formed as a part of the weight support device, but it is preferred that it be a separate and independent component so that it can be washed and reused, exchanged, or disposed of, for sanitary reasons. For ease of application, a hook strip 25 is provided. The pressure dissipation friction pad can be wrapped around the penile shaft and held in position using the hook strip to attach the free end of the felt-like backing to the adjacent portion of the the felt-like backing of the pressure dissipation pad. The hook strip can be from ¼ to 1½ inches wide and from 2 to 6 inches long.

Figure 3:
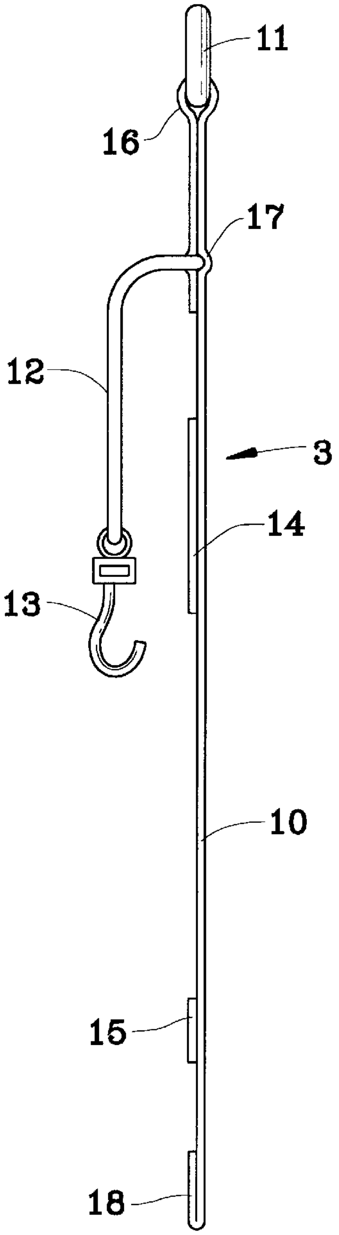
FIG. 3 is a side view of the weight supporting means of the traction device.

FIG. 3 shows a side view of the weight support device 3. The basic component is a weight attachment strap 10 that can be, for example, a woven nylon strap. A first end of the strap can be bent back upon itself and secured to form an end 18. The second end of the strap is bent back upon itself and secured so that the strap forms a loop 16 that attaches a strap buckle 11 and that can form a strap securing loop 17 for holding in place the first end of a flexible weight connector 12. While the hook 13 could be attached directly to the strap for weight attachment, it is preferred that the connector be used if the patient is to be mobile. The flexible connector is preferably from 1 to 3 inches long and can be in the shape of a doughnut or o-ring made, for example, from surgical rubber with a diameter from about 1 to 2 inches. Also secured to the weight strap 10 are a loop or felt-like securing pad 14 and a hook securing pad 15. The second end of the flexible weight connector 12 is shown secured to a weight connector hook 13. This is a standard connector type hook made of plastic or metal with an attachment eye with the hook itself rotatable with respect to the attachment eye portion of the hook. The attachment strap, whether of woven nylon, or plastic, can have a width of from ½ to 2 inches and a length of from 6 to 12 inches. The hook securing pad 15 is placed near the first end 18 of the weight attachment strap 10. The loop securing pad 14 extends along the central portion of the weight attachment strap on the same side as the hook securing pad. With this arrangement, the length of strap 10 that extends around and over the pressure dissipation pad can be adjusted. This accommodates different size shafts and permits control of the pressure exerted on the pressure dissipation pad against the shaft.

FIG. 4 shows a side view of the selective weight device 4. A set of incrementally divided base weights 40 forms the upper and lower weights. They are rounded off so as to not present sharp corners that could cause damage to the patient or objects. Additional weights 41 can be inserted between the base weights 40 to adjust the amount of force or traction transmitted to the support device 3 and the penile shaft. The weights are provided with a centrally located hole that permits the bolt 43 to pass through. An eye 42 in one end of the bolt provides a place for attachment of the weight connector hook 13 and relief weight hook 33. A passage 46 is provided in the eye 42 of the eye bolt 43 so that an elastic connector can be used or added as a shock absorbing means for a mobile patient. The weights 40,41 are added to and removed from the bolt 43 by removing the wing nut 44. A rubber or plastic cap 45 covers the end threads of the bolt 43 as a precaution against scratches, scrapes, punctures, damage to the patients clothing, adjacent objects and accidental removal of the wing nut. The weights, weight bolt, and wing nut are preferably made of stainless steel to prevent rust and make sterilization easier.

FIG. 5 is a side view of the weight relief device 5. It is made in two sections that are adjustably attached together. The basic component of the first section is a flexible adjustment strap 30 that has a first end bent back upon itself to form an attachment loop 34 to receive the relief weight hook 33. The second end of the flexible adjustment strap 30 is provided with a hook securing pad 35. This pad is similar to the attachment pad 15 on the weight attachment strap 10. The relief weight hook 33 is similar to the weight connector hook 13, but is shown with a commonly used accidental detachment prevention spring. The second section basic component is an auxiliary support strap 37 that has a first end either capable of securing the hooks of the hook securing pad 35 or that is covered with a material that is capable of securing the hooks of the hook securing pad. The second end of the strap 37 is bent back upon itself to form a strap handle 31 and an attachment loop 36 for securing in place a support loop 32. The handle 31, with the relief weight hook 33 attached to the eye 42 of bolt 43, allows the patient or an attendant to manually remove a part of or all of the weight from the support device 3. When the support loop 32 is attached to a belt or other support, the hook securing pad 35 allows the patient or an attendant to incrementally lift the weight device 4 so that any desired amount of the force being exerted onto the support device 3 can be relieved. This permits a traction force, that lays in-between the available weights, to be exerted against the penile shaft or permits an adjustment of the traction force without removing or changing a weight.

Figure 6:
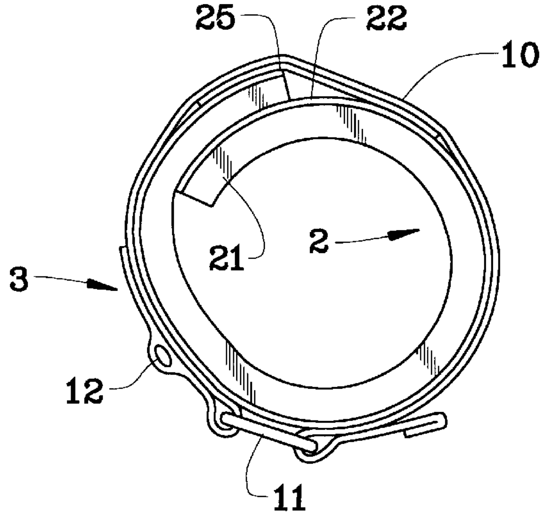
FIG. 6 is a top view of the pressure dissipation means clamped in place by the weight supporting means.

FIG. 6 is a top view of the pressure dissipation and friction device 2 being secured or clamped in place by the weight support device 3 as, for example, shown in FIG. 1. The pressure dissipation and friction device 2 is wrapped around what would be a penile shaft; the foam pad 21 with its felt-like backing 22 is held in place by the hook strip 25. The attachment strap 10 of the weight support 3 is secured around the pressure dissipation and friction device 2 to transfer the traction caused by the weights to the pressure dissipation and friction device 2. The first end 18 of the strap is threaded through the buckle 11 with the free end pulled and stretched to the desired tension. The free end is then secured to the intermediate portion of the attachment strap by engaging the hooks of pad 15 with the loop, felt or other pad 14, to hold the pressure dissipation and friction device in place. The weights are then attached to the device and force is applied to the penile shaft through the pressure dissipation pad 2.

Figure 7:
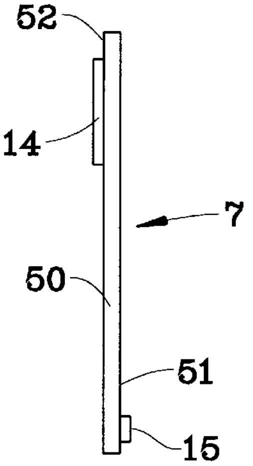
FIG. 7 and FIG. 8 are side views of a modification of the weight support means shown in FIG. 3.

FIG. 7 is a simplified but less dependable, less desirable weight attachment strap 7 that is a modification of the weight attachment strap 3 shown in FIG. 3. The weight attachment strap 7 includes a strap 50 that has a hook securing pad 15 attached to a first side first end 51 and a loop securing pad 14 extending along a second side near a second end 52. By wrapping the strap 50 around the pressure dissipation and friction device 2, the hooks of pad 15 can be secured into the securing pad 14 to hold the strap in place. With this embodiment, or the strap 10 shown in FIG. 1, a hook such as 13 can be secured directly to the strap or the strap can be threaded through the eye of the hook. The weights can then be secured directly to the hook, for immobile patient traction, or a doughnut or o-ring shaped elastic connector can be placed between the hook and weights by slipping the elastic connector over the hook and through the passage 46 in the eye 42 of the eye bolt 43 for mobile patient traction.

Figure 8:
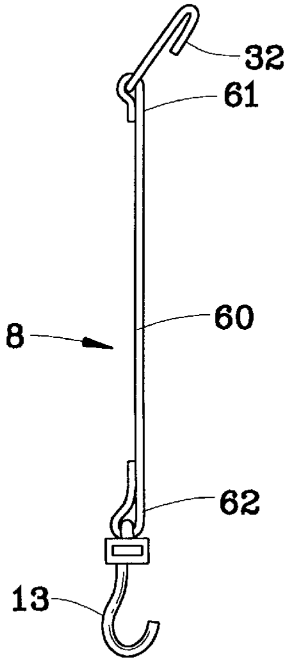

FIG. 8 is a weight connector 8 that is a modification of the flexible weight connector 12 shown in FIG. 3. A weight hook 13 is provided at a second end 62 of the flexible connector 60. A support loop 32 is provided at a first end 61 of the flexible connector so that the support loop 32 can be placed over the attachment strap 50 for securing the flexible connector 60 to the attachment strap for transferring the force exerted by the weight means to the pressure dissipation and friction pad 2. While the connector can be a resilient, woven nylon material, if desired, any of the flexible weight connection means 12, 30, 60 may be of a resilient and/or elastic material that acts more as a shock absorber than the woven type strap or connector does.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

I claim:

1. A penile traction device including:

an elongated deformable resilient pad to contact and to be wrapped around a penile shaft for frictionally gripping the shaft and for dissipating and distributing force applied to the shaft through said elongated deformable resilient pad;

said elongated deformable resilient pad having an essentially coextensive felt material backing for distributing said force throughout said elongated deformable resilient pad;

a multi-hook strip for securing said elongated deformable resilient pad in its wrapped configuration by engaging hooks of said multi-hook strip at different locations in said felt material backing;

an elongated attachment strap having a first end and a second end and a central section to be wrapped around said elongated deformable resilient pad for transferring said force to said elongated deformable resilient pad;

said elongated deformable resilient pad and said elongated attachment strap being independent from one another permitting relative movement between said elongated deformable resilient pad and said elongated attachment strap;

means for adjusting the length of said elongated attachment strap in contact with said elongated deformable resilient pad in its wrapped configuration and means for securing said elongated attachment strap at said adjusted length to control the pressure exerted on said elongated deformable resilient pad by said elongated attachment strap;

weight attachment means connected to said elongated attachment strap for attaching a weight to provide said force.

2. The penile traction device of claim 1 wherein:

said elongated deformable resilient pad is a porous foamed hypo-allergenic material.

3. The penile traction device of claim 1 wherein:

said means for adjusting the contact length of said elongated strap includes a buckle on said second end of said strap so that said first end of said strap can be threaded through said buckle for adjusting said length of said elongated strap in contact with said elongated deformable resilient pad and for adjusting the pressure exerted on said elongated deformable resilient pad.

4. The penile traction device of claim 1 wherein:

an elongated connector is positioned between said elongated attachment strap and said weight attachment means;

said elongated connector is elastic flexible and acts as a shock absorbing means when sudden movements are made.

5. The penile traction device of claim 1 wherein:

said means for securing said elongated strap in its said adjusted length includes multiple hooks.

6. The penile traction device of claim 5 wherein:

said means for adjusting the length of said elongated strap in contact with said elongated deformable resilient pad includes a buckle on said second end of said elongated strap so that said elongated strap first end can be threaded through said buckle for adjusting said length of said elongated strap in contact with and pressure exerted on said elongated deformable resilient pad.

7. The penile traction device of claim 6 wherein:

said means for securing said elongated attachment strap at said adjusted length includes a multi hook pad that includes said multiple hooks near said first end of said elongated attachment strap and an elongated hook attachment strip near said central section of said elongated attachment strap with both said multi hook pad and said elongated hook attachment strip being on the same side of said elongated attachment strap.

8. The penile traction device of claim 1 wherein:

said means for adjusting the length of said elongated attachment strap in contact with said elongated deformable resilient pad in its wrapped configuration includes a multi-hook securing pad attached on said first end on a first side of said elongated attachment strap and an elongated loop securing pad attached to said second end on a second side of said elongated attachment strap.

9. A penile traction device including:

an elongated deformable resilient pad to be wrapped around a penile shaft for frictionally gripping the shaft and for dissipating and distributing force applied to the shaft through said elongated deformable resilient pad;

an elongated attachment strap having a first end and a second end and a central section to be wrapped around said elongated deformable resilient pad for transferring said force to said elongated deformable resilient pad;

means for adjusting the length of said elongated attachment strap and means for securing said elongated attachment strap at said adjusted length;

weight attachment means connected to said elongated attachment strap for attaching a weight device to provide said force;

an adjustment strap relief means for relieving all or a portion of the force applied to said elongated attachment strap and said elongated deformable resilient pad.

10. The penile traction device of claim 9 wherein:

said adjustment strap relief means has a hand grip formed on one end and a weight attachment means on the other end for attaching a weight device.

11. The penile traction device of claim 10 wherein:

said adjustment strap relief means one end is also provided with a support loop for securing said adjustment strap relief means at a fixed selected position relative to said elongated deformable resilient pad.

12. The penile traction device of claim 10 wherein:

said weight device is attached to said weight attachment means of said adjustment strap relief means and to said weight attachment means of said elongated attachment strap;

said weight device has an elongated eye bolt with an eye on a first end of said elongated eye bolt with said eye being large enough to accommodate both said weight attachment means connected to said elongated attachment strap and said weight attachment means on said adjustment strap relief means;

a removable weight securing and release means at a second end of said elongated eye bolt for adding and removing weights from said elongated eye bolt;

a resilient cap for covering threads on said second end of said elongated eye bolt.

13. The penile traction device of claim 9 wherein:

said adjustment strap relief means is formed in two sections, a first section and a second section that are adjustable relative to one another.

14. The penile traction device of claim 13 wherein:

said adjustment strap relief means first section has a hand grip formed in a second end and an adjustment securing means formed along a first end;

said adjustment strap relief means second section has an adjustment securing means formed along a second end and a weight attachment means at a first end for attaching it to said weight means.

15. The penile traction device of claim 13 wherein:

said adjustment strap relief means first section is provided with a support loop for securing said relief means first section at a fixed selected position relative to said elongated deformable resilient pad;

said adjustment strap relief means second section includes an elongated elastic strap that transfers force and acts as a shock absorbing means when sudden movements are made.

16. The penile traction device of claim 15 wherein:

an elongated connector is provided between said elongated attachment strap and said weight attachment means;

said elongated connector is a woven material that is flexible and acts as a shock absorbing means when sudden movements are made.

17. The penile traction device of claim 13 wherein:

said adjustment strap relief means first section is provided with a support loop for securing said relief means first section at a fixed selected position relative to said elongated deformable resilient pad.

18. The penile traction device of claim 17 wherein:

said weight device is attached to both said weight attachment means connected to said elongated attachment strap and said adjustment strap relief means;

said weight device includes means for adding and subtracting weights to select the amount of force applied to said elongated connector;

said adjustment strap relief means adjustment between said adjustment strap relief means first section and second section permitting the removal of a portion of the force exerted by said weight device on said elongated attachment strap so that said force transmitted through said elongated attachment strap can be adjusted in increments between and more selective than that provided by the addition and subtraction of weights to and from said weight device.

* * * * *